United States Patent [19]

Kaneko et al.

[11] Patent Number: 5,286,856
[45] Date of Patent: Feb. 15, 1994

[54] PRODUCTION OF CRYSTALLINE PENEM

[75] Inventors: Masayoshi Kaneko, Takarazuka; Shigeo Yabuno, Osaka, both of Japan

[73] Assignee: Takeda Chemical Industries, Ltd., Osaka, Japan

[21] Appl. No.: 946,614

[22] Filed: Sep. 18, 1992

[30] Foreign Application Priority Data

Sep. 20, 1991 [JP] Japan .................................. 241648

[51] Int. Cl.$^5$ .......................................... C07D 487/04
[52] U.S. Cl. ...................................... 540/350
[58] Field of Search .................. 540/350, 310; 424/455

[56] References Cited

U.S. PATENT DOCUMENTS

| 4,029,655 | 6/1977 | Cise | 260/343 C |
| 4,990,613 | 2/1991 | Kumagai et al. | 540/350 |

FOREIGN PATENT DOCUMENTS

| 0162242 | 11/1985 | European Pat. Off. |
| 0256377 | 2/1988 | European Pat. Off. |
| 289801 | 4/1988 | European Pat. Off. |
| 0326640 | 8/1989 | European Pat. Off. |
| 54-2311 | 1/1979 | Japan |
| 56-120615 | 9/1981 | Japan |
| 1589317 | 11/1974 | United Kingdom |
| 1589316 | 11/1976 | United Kingdom |

*Primary Examiner*—Nicholas S. Rizzo
*Attorney, Agent, or Firm*—Wegner, Cantor, Mueller & Player

[57] ABSTRACT

A method of crystallizing (1R,5S,6S)-2-[(6,7-dihydro-5H-pyrazolo[1,2-a][1,2,4]triazolium-6-yl)]thio-6[(R)-1-hydroxyethyl]-1-methyl-carbapenem-3-carboxylate (hereinafter simply referred to as L-627), which is characterized by maintaining an aqueous solution of L-627 at temperatures ranging from the eutectic temperature of the solution to temperatures lower than 0° C.

The method provides some advantages that loss of L-627 accompanied by crystallization is less, number of steps in the preparation of vial formulations is less and maintenance of these steps under sterile and dust-free conditions can be performed easily, dispensation of the drug can be conducted with quantitative accuracy, and the crystals dissolve in a solvent promptly at the time of use.

21 Claims, No Drawings

PRODUCTION OF CRYSTALLINE PENEM

This invention relates to a method of providing crystalline (1R,5S,6S)-2-[(6,7-dihydro-5H-pyrazolo[1,2a][1,2,4]triazolium-6-yl]thio-6-[(R)-1-hydroxyethyl]-1-methyl-carbapenem-3-carboxylate (hereinafter simply referred to as L-627), a carbapenem antibiotic substance, excellent in solubility and also providing a vial containing the said crystalline compound.

Conventionally, crystalline L-627 filled in a vial has been provided by, for example, a method (disclosed in EP 289801, among others) which comprises dissolving L-627 by heating, subjecting the solution to filtration and sterilization, cooling the filtrate to cause crystallization, collecting the crystals by filtration, drying the crystals, then filling the crystals in the vial.

However, such conventional methods as above are accompanied by, among others, the following drawbacks, namely, (1) since L-627 decomposes when dissolved by heating or L-627 dissolved in the mother liquor does not completely precipitate as crystals when conducting crystallization, the amount of crystalline L-627 is smaller than that of L-627 actually dissolved, (2) since the number of steps is relatively large, it is difficult to maintain all of them under sterile and dust-free conditions, (3) since the filling of the drug into vials must be conduct after the drug is converted to crystalline powder, quantitatively accurate distribution is difficult as compared with the case of conducting the distribution in the state of a solution, and (4) dissolution of the crystals in the solvent at the time of use takes a relatively long time.

Circumstances being such as above, a method has been sought for providing crystals of L-627, involving reduced loss of L-627 in crystallization, reduced number of steps for providing vials containing L-627 thus easily maintaining sterility and dust-free conditions during the steps, ease of quantitatively accurate distribution of the drug and realization of prompt dissolution of crystals in a solvent at the time of use.

In view of the above-mentioned drawbacks in conventional methods, the present inventors have studied diligently and found unexpectedly that, when an aqueous solution of L-627 is maintained at temperatures ranging from eutectic temperatures to temperatures lower than 0° C., crystals of excellent solubility can be obtained, loss of L-627 accompanied by crystallization is reduced, and that, when this method of crystallization is performed in a vial, a vial containing crystalline L-627 having high solubility in a solvent at the time of use can be obtained, the process can be conducted simply and conveniently with reduced number of steps to be carried out under sterile and dust-free conditions, and the drug can be readily distributed with quantitative accuracy, thus the present invention has been accomplished.

Namely, the present invention relates to a method of crystallizing L-627, which is characterized by maintaining an aqueous solution of L-627 at temperatures ranging from the eutectic temperature of the solution to temperatures lower than 0° C.

The present invention can be conducted by maintaining an aqueous solution of L-627 at temperatures ranging from the eutectic temperatures to temperatures lower than 0° C.

The concentration of L-627 in its aqueous solution ranges usually from 0.5% (w/w) to 10% (w/w), preferably from 1% (w/w) to 5% (w/w), more preferably from 1.5% (w/w) to 2.5% (w/w). The aqueous solution is made by dissolving L-627 to distilled water at the concentration as mentioned above.

The aqueous solution of L-627 may contain for example alkaline metal halide such as sodium chloride potassium chloride, preferably sodium chloride, for increasing solbility of L-627 to water. The concentration of the alkaline metal chloride in its aqueous solution ranges usually from 0.1% (w/w) to 10% (w/w), preferably from 0.5% (w/w) to 5% (w/w), more preferably from 1% (w/w) to 3% (w/w).

The aqueous solution of L-627 may also contain an organic solvent which does not inhibit the crystallization nor exert undesirable effects on L-627. Examples of the organic solvent include water-soluble organic solvents such as $C_{1-6}$ alcohol e.g. methyl alcohol, ethyl alcohol, n-propyl alcohol and isopropyl alcohol, and $C_{3-7}$ ketone e.g. acetone. Preferable examples of the organic solvents which may be contained include $C_{1-3}$ alcohol such as methyl alcohol and ethyl alcohol, and $C_{3-5}$ ketone such as acetone, and more preferable examples include methyl alcohol, ethyl alcohol and acetone. While the concentration of these organic solvents in an aqueous solution of L-627 varies with kinds of such solvents, it usually ranges from 0.1% (v/v) to 10% (v/v), preferably from 0.5% (v/v) to 6% (v/v), more preferably, for example, from 1% (v/v) to 3% (v/v). Practically, when ethyl alcohol is employed, it is added to an aqueous solution of L-627 so that the concentration becomes preferably 0.5% (v/v) to 6% (v/v), more preferably, 1% (v/v) to 3% (v/v). These solvents are mixed preferably after L-627 is dissolved in water.

In the present invention, eutectic temperatures include eutectic point and temperatures lower than those at which eutectic crystal can be formed. Practically, in the case of using 2% aqueous solution of L-627, the eutectic temperatures mean those whose electric resistance ranges from about $10^{3.2}$ KΩ to lower than $10^{4.6}$ KΩ, more specifically $-10°$ C. to $-2°$ C.

The eutectic temperatures are influenced by the concentration of L-627 or a water-soluble organic solvent contained in the aqueous solution of L-627, and they are, generally, in the range of $-10°$ C. to $-0.5°$ C., preferably $-6°$ C. to $-1°$ C., more preferably $-4°$ C. to $-2°$ C.

The temperatures ranging from the eutectic temperatures to those lower than 0° C., at which the present invention is carried out, usually ranges from $-10°$ C. to temperatures lower than 0° C., preferablly $-6°$ C. to $-1°$ C., more preferablly $-4°$ C. to $-2°$ C. The eutectic temperatures are usually lowered by dissolving alkaline metal halide to the aqueous solution of L-627. Concretely, in the case of using a 2% ethanolic aqueous solution of L-627, the present invention can be conducted by maintaining the solution at temperatures ranging from $-10°$ C. to $-0.2°$ C., preferably $-6°$ C. to $-0.5°$ C., more preferably $-4°$ C. to $-1°$ C.

While the time during which the aqueous solution of L-627 is maintained at temperatures ranging from the eutectic temperatures to those lower than 0° C. is influenced by the concentration of L-627 or a water-soluble organic solvent contained in the aqueous solution of L-627, it ranges generally from 0.5 hour to 48 hours, preferably from 5 hours to 30 hours, more preferably from 10 hours to 20 hours.

In the crystallization method of the present invention, for performing the crystallization with higher efficiency, it is preferable to freeze the aqueous solution of L-627 prior to maintaining the solution at temperatures ranging from the eutectic temperatures to those lower than 0° C.

The frozen state means, in the measurement of conductivity, that the electric resistance of the aqueous solution of L-627 exceeds $10^{4.6}$ KΩ. While the temperature for freezing the aqueous solution varies with, for example, the concentration of L-627 or the concentration of a water-soluble organic solvent contained in the aqueous solution, it ranges usually from −40° C. to −10° C., preferably from −30° C. to −10° C., more preferably from −25° C. to −15° C. Practically, for example, in the case of using a solvent consisting of water alone, the temperature for freezing the aqueous solution ranges from −40° C. to −10° C., preferably from −30° C. to −10° C., more preferably from −25° C. to −15° C. And, in the case of, for example, using a 2% (v/v) ethanolic aqueous solution of L-627, temperatures for freezing the aqueous solution ranges from −40° C. to −10° C., preferably from −30° C. to −10° C., more preferably from −25° C. to −15° C.

The freezing may be conducted rapidly or over a period of time. The time required for the freezing varies with the concentration of L-627, the concentration of a water-soluble organic solvent contained in the aqueous solution or temperatures at the time of conducting the freezing, and it ranges generally from 0.5 hour to 48 hours, preferably from one hour to 30 hours, more preferably from one hour to 10 hours.

In the crystallization method of this invention, for performing the crystallization with higher efficiency, it is preferable to freeze an aqueous solution of L-627 after maintaining the aqueous solution at temperatures ranging from the eutectic temperatures to those lower than 0° C. The temperatures in this freezing process are influenced by the concentration of L-627 or the concentration of a water-soluble aqueous solvent contained in the aqueous solution, and they are generally within the range from −40° C. to −10° C., preferably from −30° C. to −15° C., more preferably from −25° C. to −15° C. Practically, for example, in the case of using a solvent consisting of water alone, the temperature for freezing the aqueous solution ranges from −40° C. to −10° C., preferably from −30° C. to −10° C., more preferably from −25° C. to −15° C. And, in the case of, for example, using a 2% (v/v) ethanolic aqueous solution, the aqueous solution is cooled to temperatures ranging from −40° C. to −10° C., preferably from −30° C. to −10° C., more preferably −25° C. to −15° C.

The freezing may be conducted rapidly or over a period of time. The time required for the freezing varies with the concentration of L-627, the concentration of a water-soluble organic solvent contained in the aqueous solution or temperatures at the time of conducting the freezing, and it it ranges generally from 0.5 hour to 48 hours, preferably from one hour to 30 hours, more preferably from one hour to 10 hours.

In the crystallization method of this invention, for performing the crystallization with a higher efficiency, it is preferable to repeat the above-mentioned series of steps including freezing, maintaining the temperatures ranging from eutectic temperatures to those lower than 0° C. and cooling. The frequency of the repetition varies with the concentration of L-627, the concentration of a water-soluble organic solvent contained in the aqueous solution, the temperatures when conducting freezing, those when raising temperatures and those for cooling. It ranges preferably from once to 15 times, more preferably, for example, from twice to ten times.

And, in the present invention, by conducting the above-mentioned crystallization of L-627 in a vial, drying the crystals under reduced pressure and closing the vial tightly, vials containing crystalline powder of L-627 can be provided.

Crystals obtained by conducting the above-mentioned method of this invention in vials are dried under reduced pressure in vials. The pressure employed in this process is generally 5 mmHg or less, preferably ranges from 1 mmHg to 0.1 mmHg, more preferably 0.1 mmHg to 0.5 mmHg.

The temperatures in the process of conducting the drying under reduced pressure vary with the heat of sublimation of the solvent, the concentration of L-627, the concentration of a water-soluble organic solvent contained in the aqueous solution or the pressure when drying the crystals under reduced pressure. And, for avoiding melting of the crystals, by adjusting the environmental temperatures at the initial stage at about 50° C. at the highest, the drying under reduced pressure is conducted at the preparation temperatures not exceeding the melting point of crystals of L-627, and then, after the water-content in the crystals is decreased to 6% to 8% (w/w), is conducted until the moisture in the crystals of L-627 becomes about 2% (w/w) or less while maintaining the environmental temperature at temperatures ranging from 25° C. to 50° C., preferably from 30° C. to 45° C. In the drying stage, the temperature of the preparation does not exceed the melting point of L-627 can hardly be specified, because the melting point rises when the moisture in crystals of L-627 decreases by sublimation, but it is lower than 0° C. at the initial stage of the drying under reduced pressure, and, at the time when the moisture in the crystals is reduced to 8% or less, it can be raised up to about 20° C. to 40° C.

The time required in the process of drying under reduced pressure varies with, among others, the concentration of L-627, the concentration of a water-soluble organic solvent in the aqueous solution and the pressure or the temperature when drying the crystals under reduced pressure, it usually ranges from 4 hours to 40 hours, preferably from 7 hours to 30 hours, more preferably from 10 hours to 20 hours.

In the case of conducting crystallization of the present invention in vials, it is preferable to carry out all the steps under sterile and dust-free conditions. In this case, sterilization of the aqueous solution of L-627 is conducted by sterilizing filtration. For instance, the sterilization can be performed by using, for example, a membrane filter of about 0.2 um of capability of removing minute particles. Practical examples of such membrane filters as above include nylon membrane (NR type: manufactured by Nihon Pall Ltd.) and polyvinylidene membrane (GV type: manufactured by Japan Millipore Corp.). Sterilization of containers such as vials can be conducted by, for example, steam sterilization under pressure or dry heat sterilization, preferably steam sterilization under pressure (e.g. for 15 min. to 120 min. at 100° C. to 150° C.). While dispensing of L-627 into vials is conducted preferably after dissolving L-627 into water, it can also be conducted after drying the crystals of L-627 into a powdery state. The amount to be dispensed ranges from 50 mg to 1000 mg per vial.

To state the invention in greater detail, preparation of the crystalline compound of the present invention in vials can also be conducted as follows; namely, (a) L-627 is dissolved in water,
(b) the aqueous solution of L-627 is subjected to sterilizing filtration, which is dispensed into sterilized vials,
(c) the aqueous solution of L-627 is maintained at temperatures ranging from the eutectic temperature of the solution to temperatures lower than 0° C.,
(d) the aqueous solution is dried under reduced pressure, and
(e) the vials are closed tightly.

In the above process also, it is preferable to (c') freeze the aqueous solution of L-627, before the step (c) or to (c") cool the solution, after the step (c), or to repeat a series of steps (c'), (c) and (c"). And, if desired, it is also possible to add a sterilized water-soluble organic solvent to the aqueous solution of L-627.

The vials referred to in the present invention are any vessels capable of containing a drug sealed tightly under sterile conditions, for example, vials, ampoules, etc.

The tight closure can be performed, in the case of vials, by applying a rubber stopper and by fastening with an aluminum cap, and, in the case of ampoules, by melt-sealing, etc.

L-627 and starting materials thereof can be synthesized by, for example, the method disclosed in EP 289801 or methods analogous thereto.

The crystals of L-627 obtained by the method of this invention can be used as an antibacterial agent in accordance with a conventional method, and can be safely administered, in the form of for example a vial containing its antibacterially effective amount, to mammals including man for the therapy of infectious diseases. The dosage varies widely with the agent, body weight and symptoms of the patient, dosage forms, doctor's diagnosis, etc. It ranges normally from about 200 to about 3,000 mg per day for the therapy of infectious diseases of adults (for example, infectious diseases of urinary passages, suppurative diseases, infectious diseases of respiratory organs or infectious diseases of bile duct, etc.). In general, the antibacterial agent can be administered intravenously as injection by dissolving in, for example, distilled water.

The present invention provides a method of preparing crystals of L-627, which is characterized by reduced loss of L-627 accompanying crystallization, fewer processing steps and easy maintenance of these steps under sterile and dust-free conditions, easy dispensation of the drug with quantitative accuracy, and quick dissolution of crystals in a solvent, thus providing an advantageous method of preparing L-627 injections.

REFERENCE EXAMPLE 1

In 18 ml of distilled water was dissolved 200 mg of L-627, and the solution was subjected to filtration with the membrane filter (manufactured by Japan Millipore Corp.: SLGV 025 LS). The filtrate was freeze-dried to give powdery L-627, to which was added 1.8 ml of sterilized distilled water, followed by heating up to 40° C. to dissolve L-627 completely. The aqueous solution of L-627 was left standing for 3 hours at 5° C. in a refrigerator, then resulting crystalline precipitates were collected by filtration. The crystals were washed with a small volume of a sterilized 50% (v/v) ethanolic aqueous solution. The crystals washed as above were subjected to lyophilization for 12 hours under reduced pressure not exceeding 1 mmHg while adjusting environmental temperatures to a range from 20° C. to 25° C., followed by continuing the lyophilization for 3 hours under the same inner pressure of the lyophilizer while adjusting environmental temperatures to a range of 35° C. to 40° C. After completion of the lyophilization, inner pressure of the lyophilizer was restored to normal pressure to give 152 mg (yield: 78%) of L-627 as crystals. The crystallinity of thus-obtained L-627 was confirmed under observation with a polarizing microscope.

WORKING EXAMPLE 1

In 10 ml of distilled water was dissolved 200 mg of L-627, and the solution was subjected to filtration with the membrane filter (manufactured by Japan Millipore Corp.: SLGV 025 LS). The filtrate was filled in a sterilized vial, and the vial was put in a thermostat (manufactured by NESLAB Inc.: RTE-9). The temperature of the solution was cooled to $-18°$ C. taking one hour to have the solution frozen. Then, the temperature was raised up to those ranging from $-2°$ C. to $-0.5°$ C. and this temperature range was maintained for about 2 hours, then the temperature was lowered to $-20°$ C. taking one hour. The process of this raising and lowering the temperature was repeated twice, then the inner pressure of the lyophilizer was reduced to 1 mmHg or lower. Lyophilization was conducted for 12 hours while adjusting the environmental temperatures to a range of 20° C. to 25° C. Lyophilization was further conducted for 3 hours under the same inner pressure of the lyophilizer while adjusting the environmental temperatures to a range of 35° C. to 40° C. After completion of the lyophilization, the inner pressure of the lyophilizer was restored to normal pressure to give 199 mg (yield: 99.5%) of L-627 as crystals. The crystallinity of L-627 thus obtained was confirmed under observation with a polarizing microscope.

WORKING EXAMPLE 2

In 10 ml of 2% (v/v) ethanolic aqueous solution was dissolved 200 mg of L-627, and the solution was subjected to filtration with the membrane filter (manufactured by Japan Millipore Corp.: SLGV 025 LS). The filtrate was filled in a sterilized vial, and the vial was put in a thermostat (manufactured by NESLAB Inc.: RTE-9), and the temperature of the solution was cooled to $-20°$ C. taking one hour to have the solution frozen. The temperature was raised up to those ranging from $-3°$ C. to $-0.5°$ C., and the temperature of this range was maintained for about 2 hours, then the temperature was lowered to $-18°$ C. taking one hour. The process of this raising and lowering the temperature was repeated twice, then the inner pressure of the lyophilizer was reduced to 1 mmHg or lower. Lyophilization was conducted for 12 hours while adjusting the environmental temperatures to a range of 20° C. to 25° C. Lyophilization was further conducted for 3 hours under the same inner pressure of the lyophilizer while adjusting the environmental temperatures to a range of 35° C. to 40° C. After completion of the lyophilization, the inner pressure of the lyophilizer was restored to normal pressure to give 199.2 mg (yield: 99.6%) of L-627 as crystals. The crystallinity of L-627 thus obtained was confirmed under observation with a polarizing microscope.

What we claim is:

1. A method of crystallizing (1R,5S,6S)-2-[(6,7-dihydro-5H-pyrazolo[1,2-a][1,2,4]triazolium-6yl)[thio-6-[(R)-1-hydroxyethyl]-1-methyl-carbapenem-3carboxylate, which comprises maintaining an aqueous solution of the said compound at temperatures ranging from the eutectic temperature of the solution to temperatures lower than 0° C.

2. A method according to claim 1, which comprises freezing the aqueous solution and then maintaining it at temperatures ranging from the eutectic temperature of the solution to temperatures lower than 0° C.

3. A method according to claim 1, wherein the eutectic temperature ranges from −10° C. to −2° C.

4. A method according to claim 1, which comprises maintaining the aqueous solution at temperatures ranging from the eutectic temperature of the solution to temperatures lower than 0° C. and then freezing it.

5. A method according to claim 2 or 4, wherein the freezing is conducted at −40° C. to −10° C. for 0.5 hour to 48 hours.

6. A method according to claim 1, wherein the temperature ranges from −6° C. to −1° C.

7. A method according to claim 6, wherein the temperatures ranges from −4° C. to −2° C.

8. A method according to claim 1, wherein the time of maintaining the aqueous solution at temperatures raning from the eutectic temperature of the solution to temperatures lower than 0° C. ranges from 0.5 hour to 48 hours.

9. A method according to claim 8, wherein the time ranges from 5 hours to 30 hours.

10. A method according to claim 8, wherein the time ranges from 10 hours to 20 hours.

11. A method according to claim 1, wherein the aqueous solution contains an alkaline metal halide.

12. A method according to claim 11, wherein the alkaline metal halide is sodium chloride.

13. A method according to claim 11, wherein a concentration of the alkaline metal halide in the aqueous solution is 0.1% (w/w) to 10% (w/w).

14. A method according to claim 1, wherein the aqueous solution is supplemented with an organic solvent.

15. A method according to claim 14, wherein the organic solvent is a $C_{1-6}$ alcohol or $C_{3-7}$ ketone.

16. A method according to claim 14, wherein the $C_{1-6}$ alcohol is ethanol.

17. A method according to claim 14, wherein the concentration of the organic solvent in the aqueous solution ranges from 1% (v/v) to 10% (v/v).

18. A method according to claim 1, wherein the concentration of (1R,5S,6S)-2-[(6,7-dihydro-5Hpyrazolo[1,2-a][1,2,4]triazolium-6-yl)]thio-6-[(R)-1hydroxyethyl]-1-methyl-carbapenem-3-carboxylate in the aqueous solution ranges from 0.5% (w/w) to 10% (w/w).

19. A method according to claim 18, wherein the concentration is 1.5% (w/w) to 2.5% (w/w).

20. A method according to claim 1, which comprises repeating from once to 15 times a series of steps including freezing the aqueous solution, maintaining it at temperatures ranging from the eutectic temperature of the solution to temperatures lower than 0° C. and then freezing it.

21. A method according to claim 4, wherein the freezing is conducted at −40° C. to −10° C. for 0.5 hour to 48 hours.

* * * * *

UNITED STATES PATENT AND TRADEMARK OFFICE
CERTIFICATE OF CORRECTION

PATENT NO. : 5,286,856

DATED : February 15, 1994

INVENTOR(S) : Masayoshi KANEKO et al.

It is certified that error appears in the above-identified patent and that said Letters Patent is hereby corrected as shown below:

```
Column 7 and Column 8,
 Claim 1, line 2, change "6yl)" to --6-yl);
 Claim 18, line 3, change "5Hpyrazolo" to --5H-pyrazolo--;
          line 4, change "1hydroxyethyl" to --1-hydroxyethyl--.
```

Signed and Sealed this

Sixteenth Day of August, 1994

*Attest:*

BRUCE LEHMAN

*Attesting Officer*      *Commissioner of Patents and Trademarks*